United States Patent
Maeda

(10) Patent No.: US 8,794,052 B2
(45) Date of Patent: Aug. 5, 2014

(54) LIQUID CHROMATOGRAPH

(75) Inventor: Yoshiaki Maeda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 287 days.

(21) Appl. No.: 13/259,915

(22) PCT Filed: Apr. 7, 2010

(86) PCT No.: PCT/JP2010/056310
§ 371 (c)(1),
(2), (4) Date: Sep. 23, 2011

(87) PCT Pub. No.: WO2010/119801
PCT Pub. Date: Oct. 21, 2010

(65) Prior Publication Data
US 2012/0024048 A1    Feb. 2, 2012

(30) Foreign Application Priority Data

Apr. 16, 2009    (JP) .................. 2009-100300

(51) Int. Cl.
| | | |
|---|---|---|
| *G01N 13/00* | (2006.01) | |
| *G01N 30/32* | (2006.01) | |
| *G01N 30/24* | (2006.01) | |
| *G01N 30/20* | (2006.01) | |

(52) U.S. Cl.
CPC .............. *G01N 30/24* (2013.01); *G01N 30/32* (2013.01); *G01N 30/20* (2013.01)
USPC ..................................................... 73/61.55

(58) Field of Classification Search
USPC ..................................................... 73/61.55
See application file for complete search history.

(56) References Cited

U.S. PATENT DOCUMENTS

| | | | | | |
|---|---|---|---|---|---|
| 3,915,013 | A | * | 10/1975 | Gaeke ........................ | 73/863.72 |
| 5,098,563 | A | * | 3/1992 | Xin-shen ................... | 210/198.2 |
| 5,240,603 | A | * | 8/1993 | Frank et al. ................ | 210/198.2 |
| 5,846,293 | A | * | 12/1998 | Rubey et al. ................ | 73/23.27 |
| 6,584,832 | B2 | * | 7/2003 | Petro et al. ................... | 73/61.41 |
| 7,195,229 | B2 | * | 3/2007 | Maeda ........................ | 251/205 |
| 7,596,988 | B2 | * | 10/2009 | Usowicz et al. ............ | 73/61.52 |
| 7,601,543 | B2 | * | 10/2009 | Cai et al. ..................... | 436/161 |
| 7,631,542 | B2 | * | 12/2009 | Weissgerber ............... | 73/61.56 |
| 8,196,456 | B2 | * | 6/2012 | Hochgraeber et al. ...... | 73/61.55 |

(Continued)

FOREIGN PATENT DOCUMENTS

| | | | | |
|---|---|---|---|---|
| JP | 5-223800 A | | 8/1993 | |
| JP | 05223800 | * | 8/1993 | ............ G01N 30/20 |

(Continued)

OTHER PUBLICATIONS

English Translation of International Searching Report of PCT/JP2010/056310, mailing date Jun. 15, 2010 (5 pp).

*Primary Examiner* — Lisa Caputo
*Assistant Examiner* — Philip Cotey
(74) *Attorney, Agent, or Firm* — Westerman, Hattori, Daniels & Adrian, LLP

(57) ABSTRACT

In injecting a sample sucked into a sample loop in an autosampler from an injection needle into an analytical flow path via an injection port by a mobile phase, a sending flow rate of the mobile phase is reduced from a certain flow rate determined in an analysis condition to reduce pressure applied on a joint section between the needle and the injection port to thereby reduce the sample remaining in the injection port.

5 Claims, 7 Drawing Sheets

(56) References Cited

U.S. PATENT DOCUMENTS

| | | | |
|---|---|---|---|
| 8,234,939 B2 * | 8/2012 | Maeda et al. | 73/864.21 |
| 8,375,772 B2 * | 2/2013 | Fukuda et al. | 73/61.55 |
| 2003/0052007 A1 * | 3/2003 | Paul et al. | 204/450 |
| 2003/0143123 A1 | 7/2003 | Maeda | |
| 2005/0167348 A1 * | 8/2005 | Iwata | 210/198.2 |
| 2005/0194298 A1 * | 9/2005 | Usowicz et al. | 210/98 |
| 2006/0045810 A1 * | 3/2006 | Choikhet et al. | 422/100 |
| 2006/0179924 A1 * | 8/2006 | Staples et al. | 73/61.55 |
| 2007/0084766 A1 * | 4/2007 | Ishii et al. | 210/87 |
| 2007/0287192 A1 * | 12/2007 | Usowicz et al. | 436/161 |
| 2008/0296209 A1 * | 12/2008 | Takao et al. | 210/96.1 |
| 2009/0000358 A1 * | 1/2009 | Kerkdijk | 73/61.55 |
| 2009/0044607 A1 * | 2/2009 | Hochgraeber et al. | 73/61.55 |
| 2009/0084261 A1 * | 4/2009 | Tipler et al. | 95/22 |
| 2009/0145204 A1 * | 6/2009 | Huang et al. | 73/61.55 |
| 2009/0158815 A1 * | 6/2009 | Shah et al. | 73/23.42 |
| 2009/0249860 A1 * | 10/2009 | Tanikawa | 73/23.41 |
| 2010/0037919 A1 * | 2/2010 | Doebelin et al. | 134/22.12 |
| 2010/0288025 A1 * | 11/2010 | Hochgraeber | 73/61.55 |
| 2010/0326215 A1 * | 12/2010 | Maeda et al. | 73/864.21 |
| 2011/0120213 A1 * | 5/2011 | Hirayama et al. | 73/61.55 |
| 2011/0186157 A1 * | 8/2011 | Paul et al. | 137/565.01 |
| 2011/0247405 A1 * | 10/2011 | Yasunaga et al. | 73/61.55 |
| 2012/0118049 A1 * | 5/2012 | Tipler | 73/61.56 |
| 2013/0008535 A1 * | 1/2013 | Aso et al. | 137/565.01 |

FOREIGN PATENT DOCUMENTS

| | | | | |
|---|---|---|---|---|
| JP | 5-256834 A | | 10/1993 | |
| JP | 05256834 | * | 10/1993 | G01N 30/20 |
| JP | 2003-215118 A | | 7/2003 | |
| JP | 2006-292641 A | | 10/2006 | |
| JP | 2006292641 | * | 10/2006 | G01N 30/24 |
| JP | 2006-343271 A | | 12/2006 | |
| JP | 2012117945 A | * | 6/2012 | |
| WO | 2009/041441 A1 | | 4/2009 | |
| WO | WO 2009/041441 | * | 4/2009 | G01N 1/00 |

* cited by examiner

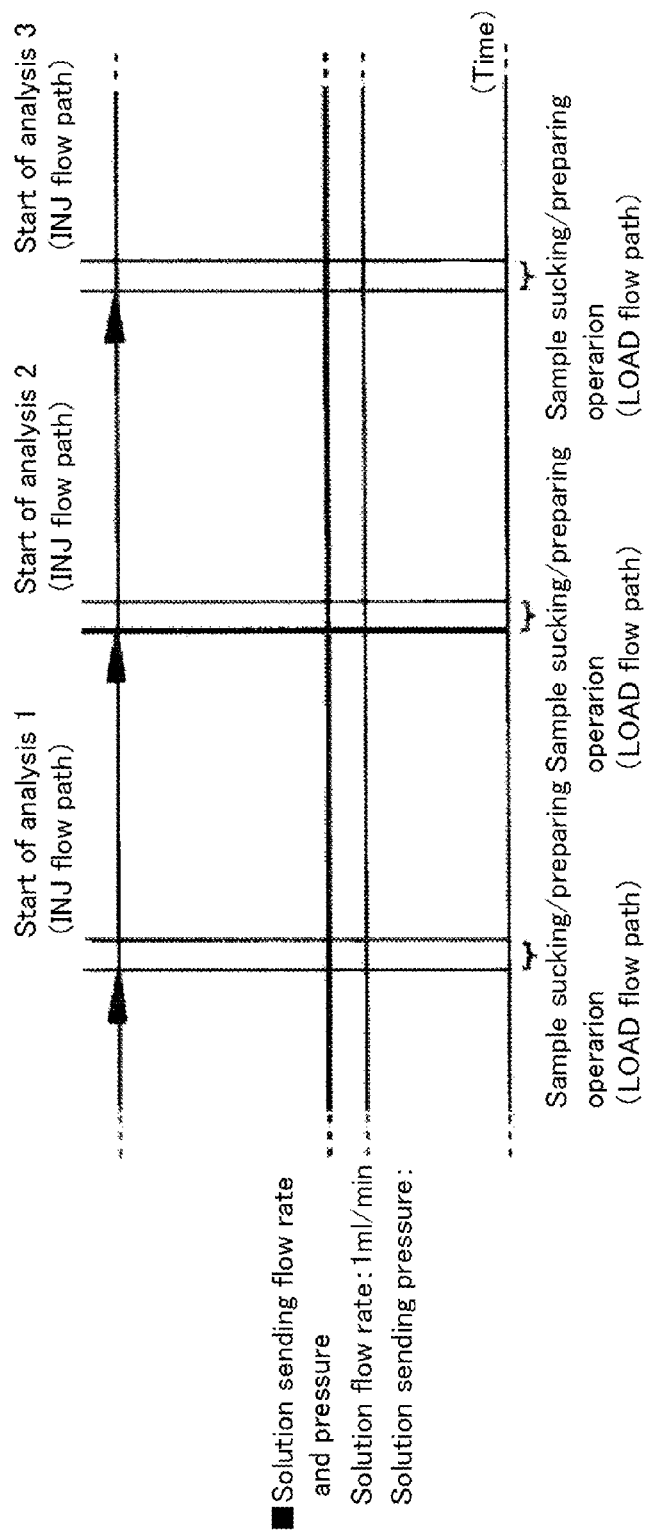

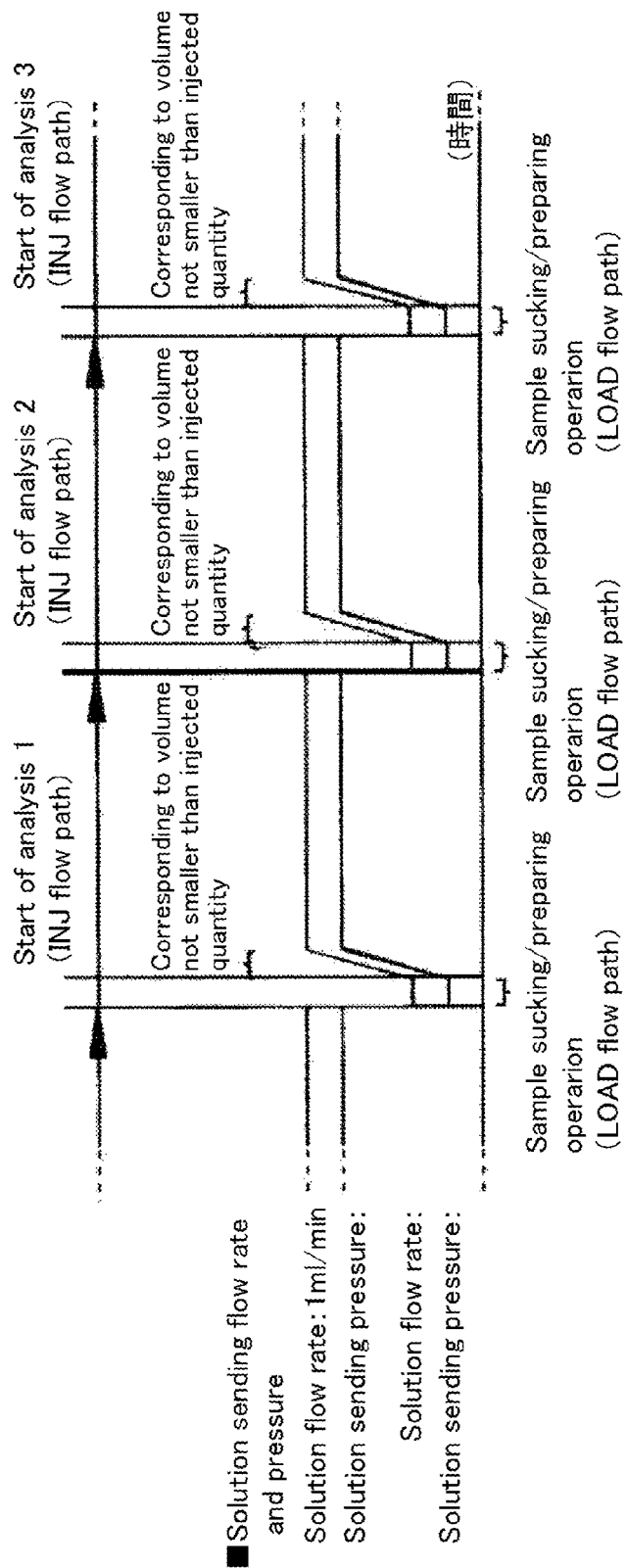

LIQUID CHROMATOGRAPH

BACKGROUND OF THE INVENTION

1. Field of the Invention

The present invention relates to a liquid chromatograph including a high-speed liquid chromatograph and particularly to a liquid chromatograph including an autosampler for injecting a sample by a whole quantity injection system.

2. Description of the Related Art

Sample injection systems of the autosampler for the high-speed liquid chromatograph can be broadly divided into two systems, i.e., a loop injection system for injecting part of a sucked sample into an analytical flow path after filling it in a sample loop and a whole quantity injection system for injecting the whole quantity of a sucked sample into an analytical flow path as it is. The whole quantity injection system is a method by which the sample is less contaminated than by the loop injection system.

In the loop injection system, an injection needle is not connected to the sample loop, and the injection needle is connected to a sucking pump to suck and discharge the sample. To introduce the sample into the sample loop, the sample is sucked into the injection needle from a sample bottle with a sucking pump, and then the injection needle is connected to an injection port to introduce the sample in the injection needle into the sample loop from the injection port. A flow path is then switched over and the sample in the sample loop is introduced into a column with a mobile phase.

On the other hand, in the whole quantity injection system, an injection needle is connected to a sample loop. After a sample in a sample bottle is sucked into the sample loop through the injection needle, the injection needle is moved from the sample bottle to an injection port, a tip end portion of the injection needle is inserted into the injection port, the injection port and the injection needle are connected, and a flow path is switched over to introduce the sample in the sample loop from the injection needle into a column via the injection port by a mobile phase.

The injection port is made up of a needle seal having a through hole at its center and a nut for retaining the needle seal. The injection needle has a tapered tip end. With the tapered portion at the tip end of the needle fitted in the hole at the center of the needle seal, the injection needle inserted into the injection port is connected so that a solution does not leak.

The present invention relates to the whole quantity injection system out of the two sample injection systems. In the whole quantity injection system, the mobile phase used when the sample in the sample loop is introduced from the injection needle into the column via the injection port with the mobile phase is the mobile phase used for analysis in the column. A flow rate of the mobile phase at this time is a set flow rate of a solvent delivery pump for constantly sending the mobile phase out to the analytical flow path and is a certain flow rate determined in an original analysis condition.

Patent Document 1: Japanese Patent Application Laid-Open No. 2006-343271
Patent Document 2: Japanese Patent Application Laid-Open No. 5-256834
Patent Document 3: Japanese Patent Application Laid-Open No. 2003-215118

If the mobile phase is sent at the certain flow rate determined by the original analysis condition in introducing the sample in the sample loop from the injection needle into the column via the injection port with the mobile phase, the sample passes through a flow path joint section between the needle and the needle seal at high pressure. Although the tapered portion at the tip end of the needle and the hole at the center of the needle seal of the injection port are fitted with each other to achieve connection without the leakage of the solution, part of the sample may remain in a small clearance between the needle and the needle seal to contaminate this portion. If this contamination occurs, it affects carry-over performance of the autosampler for the high-speed liquid chromatograph.

The problem of the part of the sample remaining in the small clearance between the needle and the needle seal becomes more pronounced on an analysis condition of high solution sending pressure of the mobile phase, such as when a high-separation column having a particle diameter of packing material of 2 μm or smaller is used as a separation column of the analytical flow path.

SUMMARY OF THE INVENTION

It is an object of the present invention to suppress carry-over due to a sample remaining in an injection port in a high-speed liquid chromatograph having an autosampler employing a whole quantity injection system.

In the present invention, in injecting a sample sucked into a sample loop in an autosampler from an injection needle into an analytical flow path through an injection port by a mobile phase, a solution sending flow rate of the mobile phase is reduced from a certain flow rate determined in an analysis condition to reduce pressure applied on a joint section between the needle and the injection port to thereby reduce the sample remaining in the injection port.

To achieve the object, a liquid chromatograph in the invention includes: an analytical flow path including a column disposed on a flow path for a mobile phase to separate an introduced sample into components and a detector for detecting sample components separated by the column; a mobile phase sending section for supplying the mobile phase with a solvent delivery pump; an autosampler; and a flow rate control section for controlling operation of the solvent delivery pump in synchronization with operation of the autosampler.

The autosampler includes an injection needle, a sample loop having one end connected to the injection needle, an injection port, a metering pump, and a flow path switching valve. The autosampler is switched between a sample sucking mode in which the flow path switching valve connects the other end of the sample loop to the metering pump to take the sample into the sample loop from the injection needle and a sample introducing mode in which the flow path switching valve connects the other end of the sample loop to the mobile phase sending section and connects the injection needle from the injection port to the analytical flow path to introduce a whole quantity of the sample sucked in the sample sucking mode into the analytical flow path by the mobile phase.

The flow rate control section has two set flow rates as flow rate set values of the solvent delivery pump, i.e., the first flow rate for separating the sample components in the analytical flow path and the lower second flow rate and controls the operation of the solvent delivery pump so that the flow rate is the first flow rate at a time for which the sample components are eluted in the analytical flow path and that the flow rate is the second flow rate at a time for which the whole quantity of the sample sucked in the sample sucking mode passes through the injection port in the sample introducing mode of the autosampler.

Although the second flow rate is preferably small for the purpose of suppressing the sample remaining in the injection port, it takes longer to introduce the sample sucked in the sample loop into the analytical flow path to reduce an operation rate of the liquid chromatograph, if the second flow rate is excessively small. On the other hand, if the second flow rate is close to the first flow rate, an effect of reducing the sample remaining in the injection port reduces. The remaining of the sample depends on a degree of fitting of a tapered portion of a tip end of the needle and a central hole in a needle seal of the injection port with each other, and therefore, it is preferable to determine such a value of the second flow rate that the carry-over due to the remaining sample does not affect the analysis result by experiments.

Although the second flow rate is 0.2 ml/minute when the first flow rate is 1 ml/minute in the example, the value is just an example. A reasonably higher second flow rate may be set in order to give a higher priority to the operation rate, if the carry-over does not become a problem.

The flow rate control section can automatically calculate a time for which the solvent delivery pump operates at the second flow rate after the flow path switching valve is switched to the sample introducing mode from a sample sucking quantity into the sample loop and the set second flow rate. If the time for which the solvent delivery pump operates at the second flow rate becomes shorter than the time for which the whole quantity of the sample sucking quantity into the sample loop passes through the injection port, the sample may remain in a clearance in the injection port. On the other hand, if the time for which the solvent delivery pump operates at the second flow rate becomes longer than the time for which the whole quantity of the sample sucking quantity into the sample loop passes through the injection port, the sample does not remain in the clearance in the injection port while an analysis time becomes long to reduce the operation rate of the liquid chromatograph. Because the time for which the whole quantity of the sample sucking quantity passes through the injection port can be obtained from the sample sucking quantity and the set second flow rate, the flow rate control section can carry out calculation and control to thereby lessen a burden of an operator. In practice, the time for which the solvent delivery pump operates at the second flow rate is preferably set by adding some extra time to the time obtained by calculation from the sample sucking quantity and the set second flow rate.

The flow rate control section may switch the flow rate of the mobile phase by the solvent delivery pump from the first flow rate to the second flow rate before switching the autosampler to the sample sucking mode for the next sample when analysis of one sample is finished.

The flow rate control section may switch the flow rate of the mobile phase by the solvent delivery pump from the first flow rate to the second flow rate before switching the autosampler to the sample sucking mode for the next sample when peak elution of one sample is finished. This is because the flow rate of the mobile phase may not be the flow rate set as the analysis condition, if the peak elution is finished.

Preferably, the injection port is directly incorporated in the flow path switching valve in the autosampler in order to reduce dead volume in the flow path switching valve.

The flow path switching valve is switched after a temporarily closed state of a flow path system. In the closed state of the flow path system, pressure in the flow path before the valve increases, if the solvent delivery pump for the mobile phase is sending the solution at the constant flow rate. Therefore, a bypass provided in the valve portion or a bumper provided in the flow path before the valve is known to suppress the pressure rise. In the invention as well, such a means of suppressing the pressure rise may be provided. As another means of suppressing such a pressure rise, there is proposed a constant pressure control method, which is not directly related to the invention. In this constant pressure control method, two control modes, i.e., constant flow rate control and constant pressure control are provided and a pump is controlled at constant pressure so that pressure on a pump outlet side is constant for a period for which a flow path is temporarily closed to switch the valve. Throughout a period for which the flow path is not closed, the pump is controlled so that the flow rate is constant. In switching to the constant pressure control, the pump is controlled at the pressure in the constant flow rate control so that pressure fluctuation does not occur in this period (see Patent Document 2).

The period for which the pump is controlled at the constant pressure by the constant pressure control method is the period for which the flow path is closed to switch the valve. The invention is aimed at a period in which the switching of the valve has been finished and the flow path is open and is not aimed at the period for which the flow path is closed. The constant pressure control method carries out the constant flow rate control throughout the period for which the flow path is open, which corresponds to the control only at the first flow rate in the invention and the method does not switch the flow rate between the first flow rate and the second flow rate in the period for which the flow path is open as in the invention.

In the liquid chromatograph in the invention, the sample passes at low pressure through the flow path joint section between the needle and the needle seal in the autosampler for automatically taking in the liquid sample and introducing it into the analytical flow path, and therefore, it is less likely that part of the sample remains in the small clearance between the needle and the needle seal to contaminate this portion. This effect is remarkable especially in a case of an analysis condition in which solution sending pressure of the mobile phase is high, e.g., when a high-separation column using packing material a particle diameter of which is as small as 2 μm or smaller is used.

BRIEF DESCRIPTION OF THE DRAWINGS

FIG. 6A is a timing diagram showing operation of prior art.

FIG. 6B is a timing diagram showing operation of the example.

DETAILED DESCRIPTION OF THE INVENTION

Figure 1:
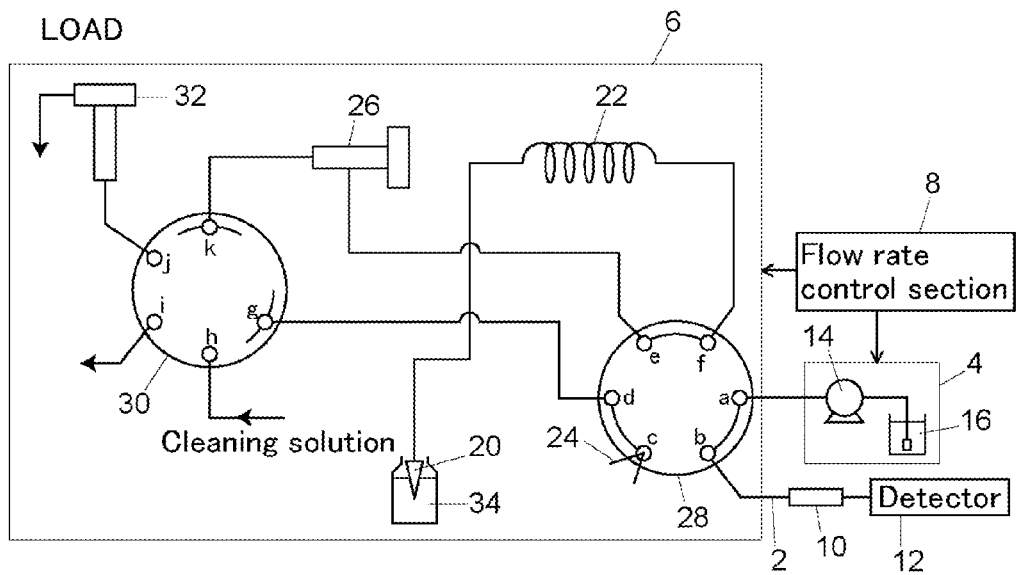
FIG. 1 is a flow path diagram showing an example in a sample sucking mode.

FIG. 1 shows the high-speed liquid chromatograph in an example in a sample sucking mode (LOAD). The high-speed liquid chromatograph includes an analytical flow path 2, a mobile phase sending section 4, an autosampler 6, and a flow rate control section 8.

The analytical flow path 2 includes an analytical column 10 disposed on a flow path of a mobile phase to separate an introduced sample into components and a detector 12 for detecting components of the sample separated by the column 10. As the detector 12, an ultraviolet absorptiometer or a mass spectrometer may be used.

The mobile phase sending section 4 supplies the mobile phase 16 in a mobile phase vessel with a solvent delivery pump 14.

The autosampler 6 includes an injection needle 20, a sample loop 22, an injection port 24, a metering pump 26, and a flow path switching valve 28.

The injection needle 20 is connected to a tip end of the sample loop 22. The injection needle 20 is retained on a transfer mechanism (not shown). The injection needle 20 is moved by the transfer mechanism between a position where it is immersed in the sample 34 in the sample vessel, a position where it is inserted into the injection port 24, and a position where it is inserted into a cleaning port 32.

Figure 2:
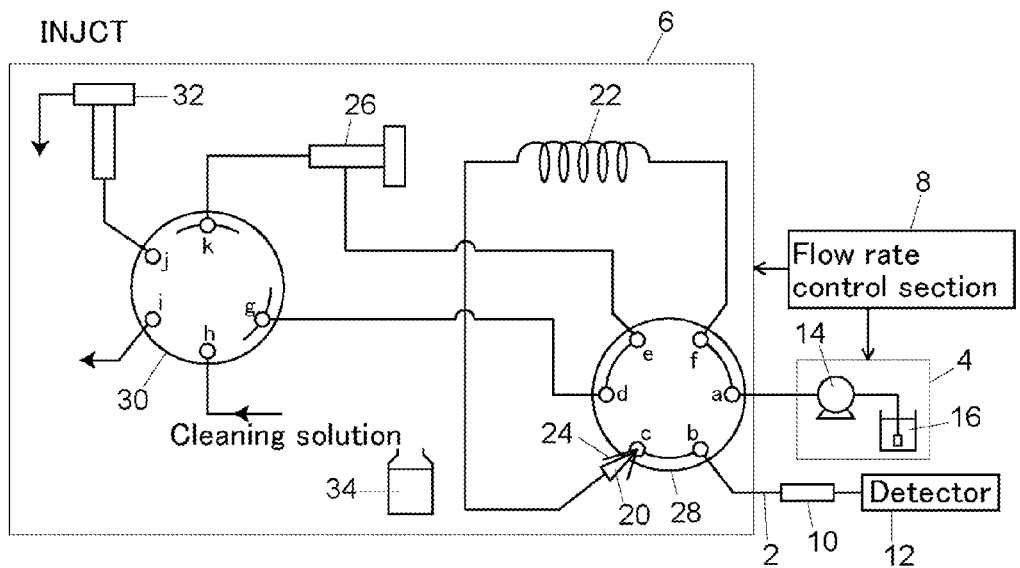
FIG. 2 is a flow path diagram showing the example in a sample introducing mode.

The flow path switching valve 28 is a high-pressure valve, has six ports a to f in a stator, and can be switched between a state in FIG. 1 in which the ports a and b are connected, the ports c and d are connected, and the ports e and f are connected and a state in FIG. 2 in which the ports f and a are connected, the ports b and c are connected, and the ports d and e are connected by rotation of a rotor.

The port a is connected to a downstream side of the solvent delivery pump 14 of the mobile phase sending section 4. The port b is connected to an inlet of the column 10 of the analytical flow path 2. The injection port 24 is connected to the port c. The port d is connected to a port g of a low-pressure valve 30. The port e is connected to one end of the metering pump 26. The port f is connected to a base end of the sample loop 22.

The low-pressure valve 30 has five ports in a stator and can connect adjacent ports by rotation of a rotor. The port h is connected to a vessel containing a cleaning solution, and the cleaning solution can be sucked from the port h. The port i is connected to a manual syringe for taking in the cleaning solution at start-up of the device or when the kind of the cleaning solution is changed. The port j is connected to the cleaning port 32.

The injection port 24 may be connected to the port c of the valve 28 by a flow path. However, in the example, a structure shown in FIG. 2 in the Patent Document 3 is employed and the injection port 24 is directly incorporated into the valve 28 in order to reduce dead volume. The Patent Document 3 is incorporated herein by reference. The injection port 24 is disposed so that a connecting port 52 is directed upward as shown in FIG. 4.

Figure 4:
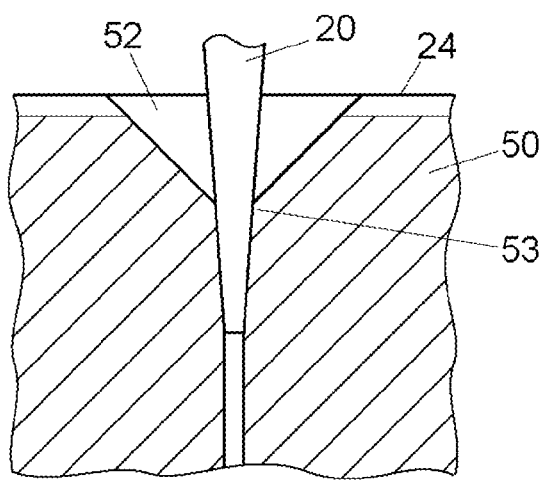
FIG. 4 is an enlarged sectional view showing an injection port portion in the example.

The injection port 24 is made up of a needle seal 50 having, at a center thereof, a through hole communicating with an opening of the connecting port 52 and a nut (not shown) for retaining the needle seal 50 as partially shown in FIG. 4. A tapered portion at a tip end of the injection needle 20 inserted from the opening 52 into the injection port 24 is fitted in the central hole in the needle seal 50 to achieve connection without a leakage of the solution. The central hole in the needle seal 50 directly communicates with a sliding face of the valve 28 through a path passing through packing or the stator of the valve 28 and the sample solution can reach the column 10 by the shortest way from the injection needle 20 when the flow path is switched.

FIG. 4 shows a state in which the needle 20 is inserted into the injection port 24 and the flow paths are connected. In this state, the sample is sent out from the needle 20, passes through the injection port 24, and flows into the flow path in the valve 28. At this time, a small clearance may be formed in a joint section between the needle 20 and the needle seal 50. When the sample is injected from the needle 20, the column 10 is connected to a downstream side of the flow path in the needle seal 50 and therefore pressure is applied on the flow path in the injection port 24 connected to the needle 20. Especially when the column 10 is a high-separation column using minute packing material a particle diameter of which is as small as 2 μm or smaller, the solution sending pressure becomes high, if the mobile phase is supplied to the column 10 at a solution sending flow rate in an analysis condition. If the sample is sent at the solution sending flow rate in the analysis condition when the sample is injected from the needle 20, the pressure is applied on the joint section between the injection port 24 and the needle 20, and there is a high possibility that part of the sample remains in the small clearance 53 between the injection port 24 and the needle 20. The remaining sample may become a source of contamination of the next sample to affect carry-over performance.

If the flow path switching valve 28 is brought into the state in FIG. 1, the sample sucking mode (LOAD) is selected. At this time, a base end portion of the sample loop 22 is connected to the metering pump 26. If the injection needle 20 is immersed in the sample 34 in the sample vessel, the sample 34 can be sucked into the sample loop 22 from the injection needle 20 by the metering pump 26.

If the flow path switching valve 28 is brought into a state in FIG. 2, the sample introducing mode (INJCT) is selected. At this time, if the base end portion of the sample loop 22 is connected to the solvent delivery pump 14 of the mobile phase sending section 4 and the injection needle 20 is connected to the injection port 24, a whole quantity of the sample taken from the injection port 24 into the analytical flow path 2 in the sample sucking mode can be introduced into the column 10 by the mobile phase.

Figure 3:
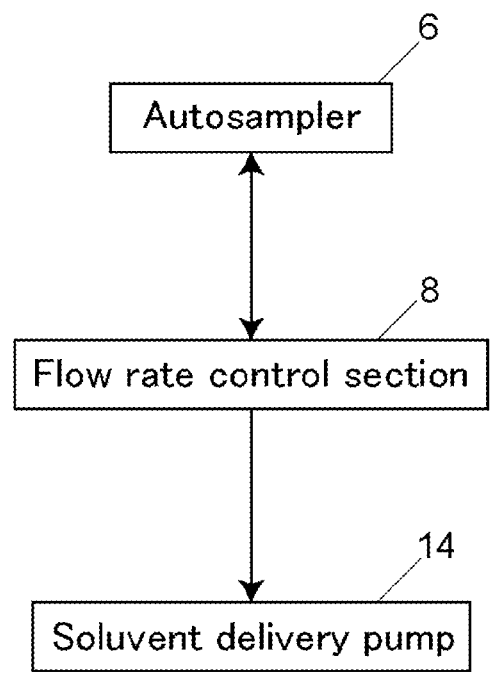
FIG. 3 is a block diagram showing a control section in the example.

As shown in FIG. 3, the flow rate control section 8 controls operation of the solvent delivery pump 14 in synchronization with operation of the autosampler 6. The flow rate control section 8 is implemented by a system controller or a workstation which is a computer.

In the flow rate control section 8, two flow rates, i.e., a first flow rate for carrying out separation of the sample components in the analytical flow path 2 and a second flow rate lower than the first flow rate are set as flow rate set values of the solvent delivery pump 14. The flow rate control section 8 controls the operation of the solvent delivery pump 14 so that the flow rate of the solvent delivery pump 14 is the first flow rate at a time for which the sample components are eluted in the analytical flow path 2 and is the second flow rate at a time for which the whole quantity of the sample sucked in the sample sucking mode passes through the injection port 24 in the sample introducing mode of the autosampler 6.

The flow rate control section 8 automatically calculates time from when the flow path switching valve 28 is switched to the sample introducing mode to start analysis till when the solvent delivery pump 14 is caused to operate at the second flow rate based on a sample sucking quantity by the autosampler 6 and the set second flow rate.

When the analysis of one sample is finished, the flow rate control section 8 may switch the flow rate of the mobile phase by the solvent delivery pump 14 from the first flow rate to the second flow rate before the autosampler 6 is switched to the sample sucking mode for the next sample. Alternatively, when peak elution of one sample is finished, the flow rate control section 8 may switch the flow rate of the mobile phase by the solvent delivery pump 14 from the first flow rate to the second flow rate before the autosampler 6 is switched to the sample sucking mode for the next sample.

Figure 5:
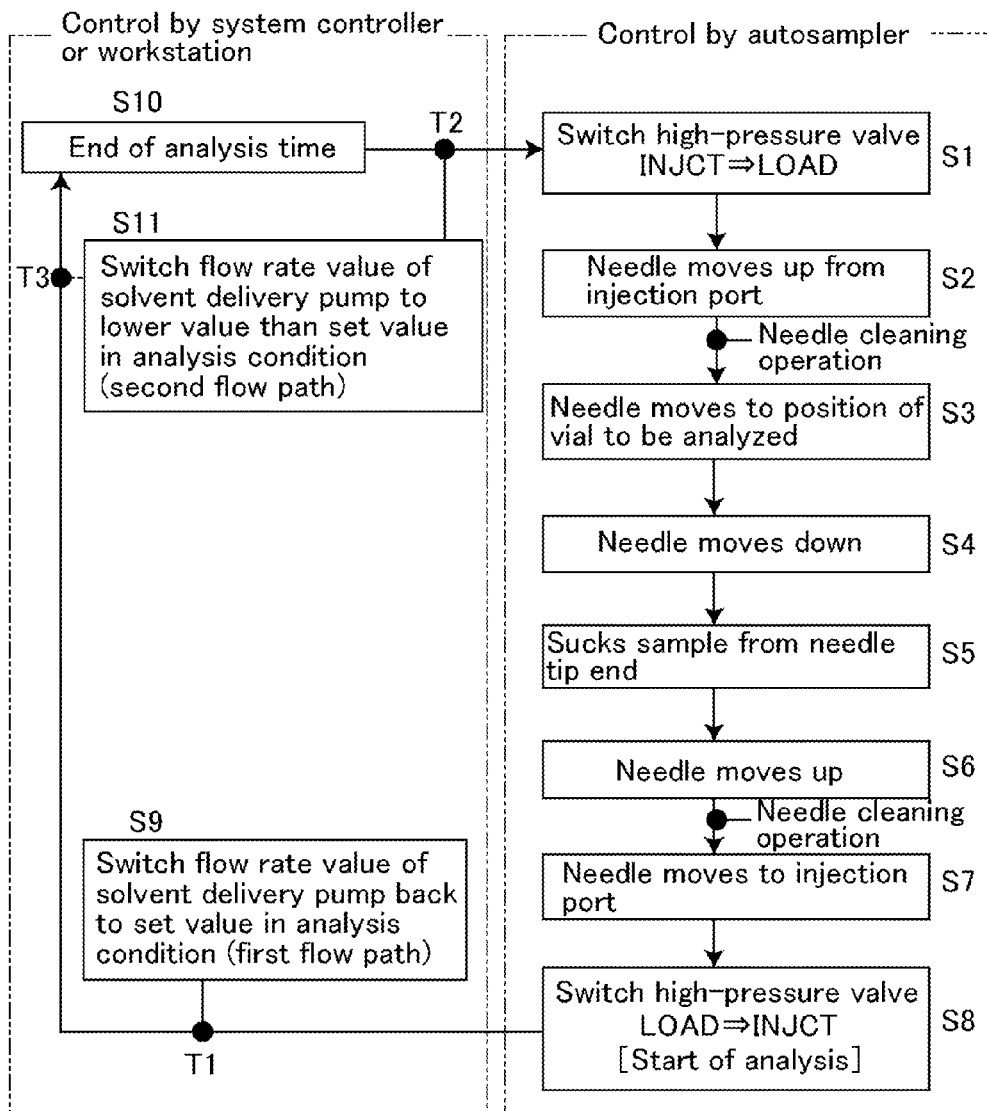
FIG. 5 is a flowchart showing operation in the example.

Next, operation of the example will be described. In FIG. 5, the operation is divided into a control on the side of the flow rate control section 8 (left side in the drawing) achieved by the system controller or the workstation and a control by the autosampler 6 itself (right side in the drawing) while the controls are correlated with each other.

Operation at a time of start of analysis of the first sample or at a time when analysis of a previous sample has been finished and analysis of the next sample is started will be described. The autosampler 6 brings the valve 28 into the state in FIG. 1 (step S1). At this time, the flow rate control section 8 carries out the control so that the flow rate value of the solvent delivery pump 14 is the second flow rate lower than the first flow rate in the analysis condition.

The autosampler 6 pulls the needle 20 out of the injection port 24, moves up the needle 20 and inserts it into the cleaning port 32 (step S2), and cleans an outside of a tip end portion of the needle 20 in the cleaning port 32.

When the cleaning of the needle 20 is finished, the autosampler 6 moves the needle 20 to a position of a vial (sample vessel) to be analyzed (step S3), moves down the needle 20 and immerses the tip end of the needle 20 in the sample 34 in the vial as shown in FIG. 1 (step S4), and actuates the metering pump 24 to take a predetermined amount of the sample 34 from the needle 20 into the sample loop 22 (step S5).

Next, the autosampler 6 moves up the needle 20 from the vial (step S6), inserts the needle 20 into the cleaning port 32, and cleans the outside of the tip end portion of the needle 20.

When the cleaning of the needle 20 is finished, the autosampler 6 moves the needle 20 to the injection port 24, and inserts the needle 20 into the injection port 24 (step S7). Then, the autosampler 6 switches the valve 28 into the state in FIG. 2 to start the analysis (step S8). As a result, the sucked sample in the sample loop 22 is pushed out by the mobile phase sent from the solvent delivery pump 14 and is introduced into the analytical flow path 2 from the needle 20 via the injection port 24. At this time, the flow rate of the solvent delivery pump 14 is the lower flow rate (second flow rate) than the solution sending flow rate (first flow rate) for the analysis condition.

The flow rate control section 8 times a time from the start of the analysis. If the flow rate control section 8 detects that the time has reached a time T1 for which the whole sucked sample passes through the injection port 24, it turns the flow rate of the solvent delivery pump 14 back to the set flow rate (first flow rate) for the analysis condition (step S9). The time T1 from the start of the analysis to the flow rate of the solvent delivery pump 14 is turned back is calculated by the flow rate control section 8 from the sample quantity sucked from the sample loop 22 and the low flow rate (second flow rate) of the solvent delivery pump 14 and maintained by the flow rate control section 8, and the flow rate control section 8 compares the timed time and the maintained time T1 and detects that the time T1 has elapsed.

By supplying the mobile phase on the flow rate condition, the sample is introduced into the column 10 and separated and the eluted sample components are detected by the detector 12. If the flow rate control section 8 detects that the time since the start of the analysis has reached the time T2 for a finish of the analysis (step S10), it switches the flow rate value of the solvent delivery pump 14 to the second flow rate value lower than the flow rate value set in the analysis condition (step S11). The analysis finish time is input as the analysis condition and set in the flow rate control section 8 or another portion of the system controller or the workstation, and the flow rate control section 8 compares the timed time and the set analysis finish time with each other and detects that the analysis finish time has been reached.

The autosampler 6 then switches the valve 28 to the state in FIG. 1 to prepare for the analysis of the next sample.

The cleaning solution is supplied to the cleaning port 32 at a time of cleaning of the needle 20 or periodically. The cleaning solution is supplied from a lower end of the cleaning port 32 and overflows from an opening in an upper end of the cleaning port 32 and is discharged. To supply the cleaning solution to the cleaning port 32, the autosampler 6 switches the valve 30 so that the port h connected to the cleaning solution is connected to the port g and that the ports j and k are connected and switches the valve 28 to the state in FIG. 2. Then, the autosampler 6 takes in the cleaning solution with the metering pump 26 and supplies it to the cleaning port 32.

The analysis is continued at the first flow rate of the mobile phase on the analysis condition and the flow rate of the solvent delivery pump may be switched to the lower second flow rate than that in the analysis condition at the time point (T3) when the elution of the sample peak is finished in the column even before the end of the analysis time. This is because the flow rate of the mobile phase is not important when the elution is finished.

FIGS. 6A and 6B show variations of the solution sending flow rate and the solution sending pressure of the mobile phase over time. FIG. 6A shows an analysis sequence for carrying out the analysis at the same set flow rate (first flow rate) both in the injection of the sample from the injection port and in the analysis. On the other hand, FIG. 6B shows an analysis sequence in the example for lowering the solution sending flow rate to the second flow rate in the injection of the sample as described by using FIG. 5.

Specific analysis results will be shown. Measurement was carried out based on an operation sequence shown in the flowchart in FIG. 5. A sample was a caffeine aqueous solution (250 mg/L) and a mobile phase was a solution containing water:methanol=70:30. The cleaning solution was water and a blank solution was the mobile phase. The set flow rate (first flow rate) of the solution sending flow rate of the mobile phase by the solvent delivery pump 14 in the analysis was 1 ml/minute. The solution sending flow rate of the mobile phase by the solvent delivery pump 14 in injecting the sample from the injection port was maintained at the set flow rate in the analysis in prior art and was the lower flow rate (second flow rate) of 0.2 ml/minute in the example. In the example, the solution sending flow rate of the mobile phase was lowered to the lower flow rate (second flow rate) for 0.1 minute since the start of the analysis (from when the valve 28 was switched to the state in FIG. 2) and for 4.5 minutes before the finish of the analysis.

Figure 7A:
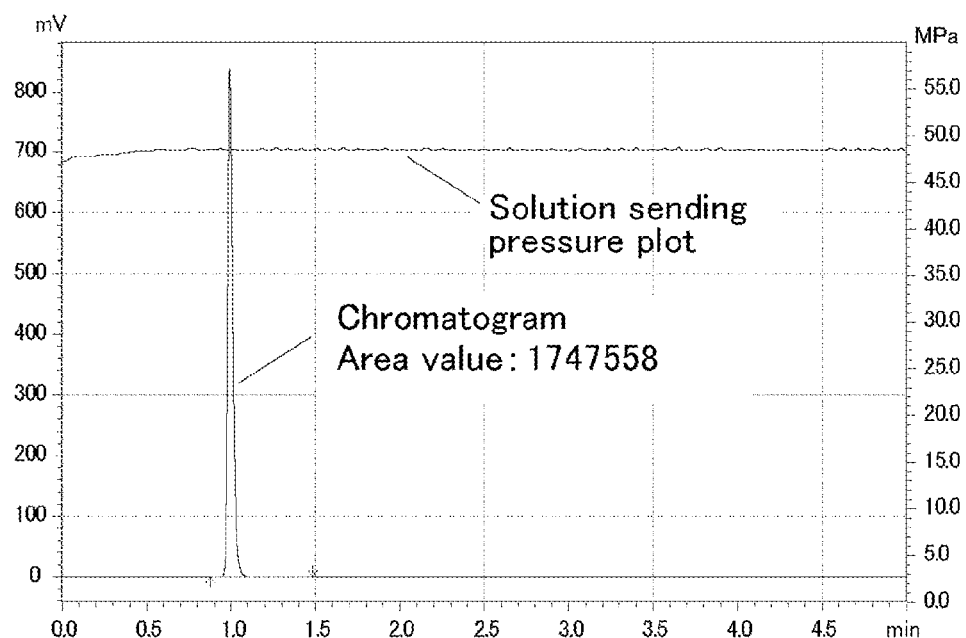
FIG. 7A is a graph showing a measurement result by a prior-art liquid chromatograph at the time of injection of a sample.
Figure 7B:
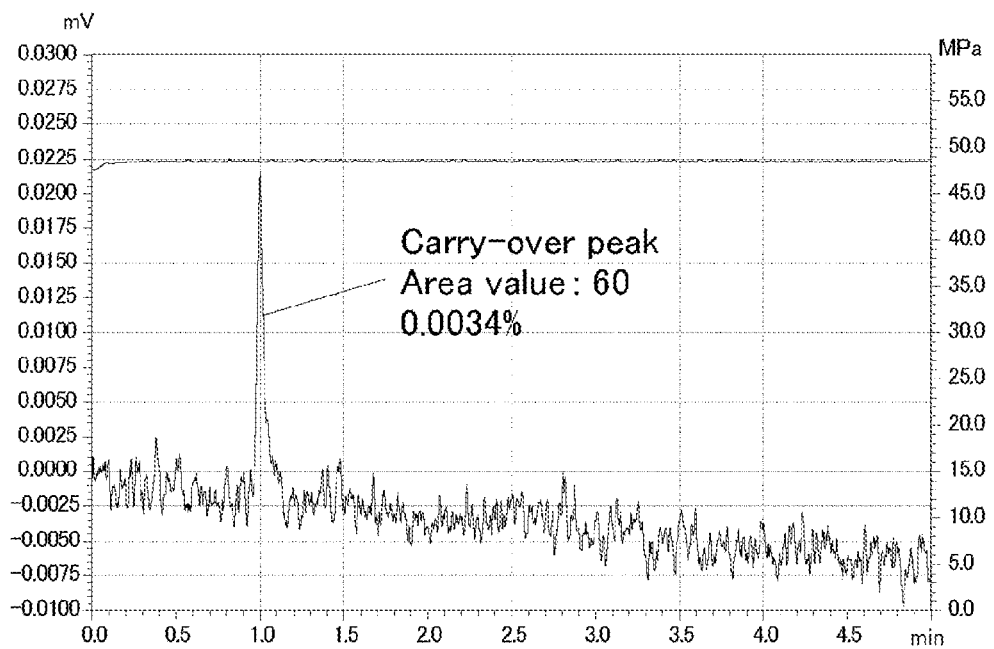
FIG. 7B is a graph showing a measurement result by the prior-art liquid chromatograph at the time of injection of a blank.

FIGS. 7A and 7B show chromatograms and measurement results of carry-over according to a prior-art method in which the solution sending flow rate of the mobile phase in injecting the sample from the injection port is the same as that in the analysis condition. A solution sending pressure plot shows that the solution sending pressure was constant solution sending pressure at the solution sending flow rate in the analysis condition throughout all segments. FIG. 7A shows a case of measurement of the sample. A peak of the caffeine was detected at a specific position. FIG. 7B shows the result when the mobile phase, instead of the sample, was injected from the injection port on the same condition to carry out blank measurement immediately after the sample analysis. Ideally, no peak was detected in the blank measurement. In this case, however, a peak of the caffeine was detected. An area value corresponds to 0.0034% of the sample. This is a peak due to the carry-over which would cause a measurement error included in a chromatogram of the next sample in normal analysis.

Figure 8A:
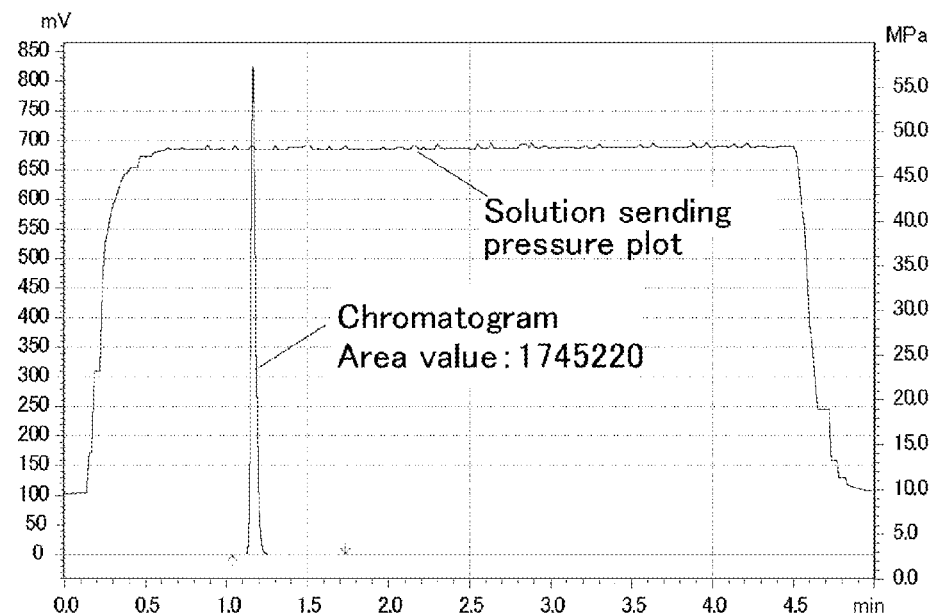
FIG. 8A is a graph showing a measurement result by a liquid chromatograph in the example at the time of injection of a sample.
Figure 8B:
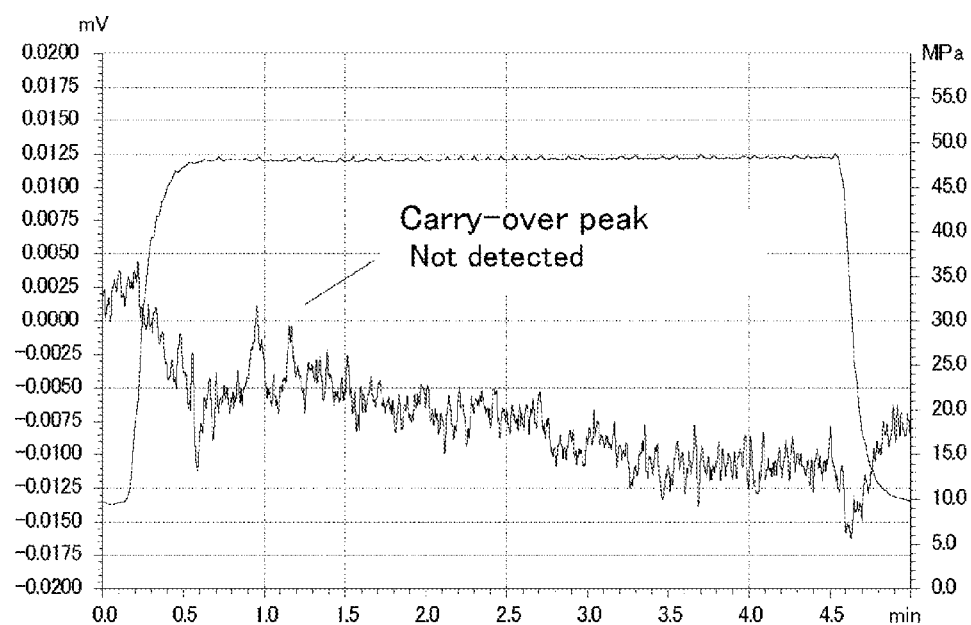
FIG. 8B is a graph showing a measurement result by the liquid chromatograph in the example at the time of injection of a blank.

On the other hand, FIGS. 8A and 8B show measurement results according to the example. The analysis condition was as described above. The injection pressure of the sample passing through the injection port was reduced by reducing the solution sending flow rate of the mobile phase in injecting the sample from the injection port and the solution sending flow rate was turned back to the set solution sending flow rate in the analysis condition after all the sample passed through the injection port. FIG. 8A shows the result of measurement of the sample, and FIG. 8B shows the result of blank measurement immediately after the measurement of the sample. According to the results in FIGS. 8A and 8B, a peak due to carry-over was not detected in the blank measurement.

From the measurement results in FIGS. 8A and 8B, it is clear that the invention can suppress the error due to the carry-over and reduction in precision of analysis.

DESCRIPTION OF THE REFERENCE NUMERALS 2 analytical flow path
4 mobile phase sending section
6 autosampler
8 flow rate control section
10 analytical column
12 detector
14 solvent delivery pump
20 injection needle
22 sample loop
24 injection port
26 metering pump
28 flow path switching valve

The invention claimed is:

1. A liquid chromatograph comprising:
an analytical flow path including a column disposed on a flow path for a mobile phase to separate an introduced sample into components and a detector for detecting sample components separated by the column;
a mobile phase sending section for supplying the mobile phase with a solvent delivery pump;
an autosampler including an injection needle, a sample loop having one end connected to the injection needle, an injection port, a metering pump, and a flow path switching valve, and being configured to be switched between a sample sucking mode and a sample introducing mode, the sample sucking mode being a mode in which the flow path switching valve connects the other end of the sample loop to the metering pump to suck the sample into the sample loop from the injection needle, and the sample introducing mode being a mode in which the flow path switching valve connects the other end of the sample loop to the mobile phase sending section and connects the injection needle from the injection port to the analytical flow path to introduce a whole quantity of the sample sucked in the sample sucking mode into the analytical flow path by the mobile phase; and
a flow rate control section for controlling operation of the solvent delivery pump in synchronization with operation of the autosampler,
wherein the flow rate control section has a first flow rate for separating the sample components in the analytical flow path and a second flow rate being lower than the first flow rate as flow rate set values of the solvent delivery pump, and
wherein the flow rate control section controls the solvent delivery pump so that the flow rate is the first flow rate at a time for which the sample components are eluted in the analytical flow path and that the flow rate is the second flow rate at a time for which the whole quantity of the sample sucked in the sample sucking mode passes through the injection port in the sample introducing mode of the autosampler.

2. The liquid chromatograph according to claim 1, wherein the flow rate control section automatically calculates a time for which the solvent delivery pump operates at the second flow rate after the flow path switching valve is switched to the sample introducing mode from a sample sucking quantity into the sample loop and the set second flow rate.

3. The liquid chromatograph according to claim 1, wherein the flow rate control section switches the flow rate of the mobile phase by the solvent delivery pump from the first flow rate to the second flow rate when analysis of one sample is finished and before switching the autosampler to the sample sucking mode for the next sample.

4. The liquid chromatograph according to claim 1, wherein the flow rate control section switches the flow rate of the mobile phase by the solvent delivery pump from the first flow rate to the second flow rate when peak elution of one sample is finished and before switching the autosampler to the sample sucking mode for the next sample.

5. The liquid chromatograph according to claim 1, wherein the injection port is directly incorporated in the flow path switching valve in the autosampler.

* * * * *